Figure 1:
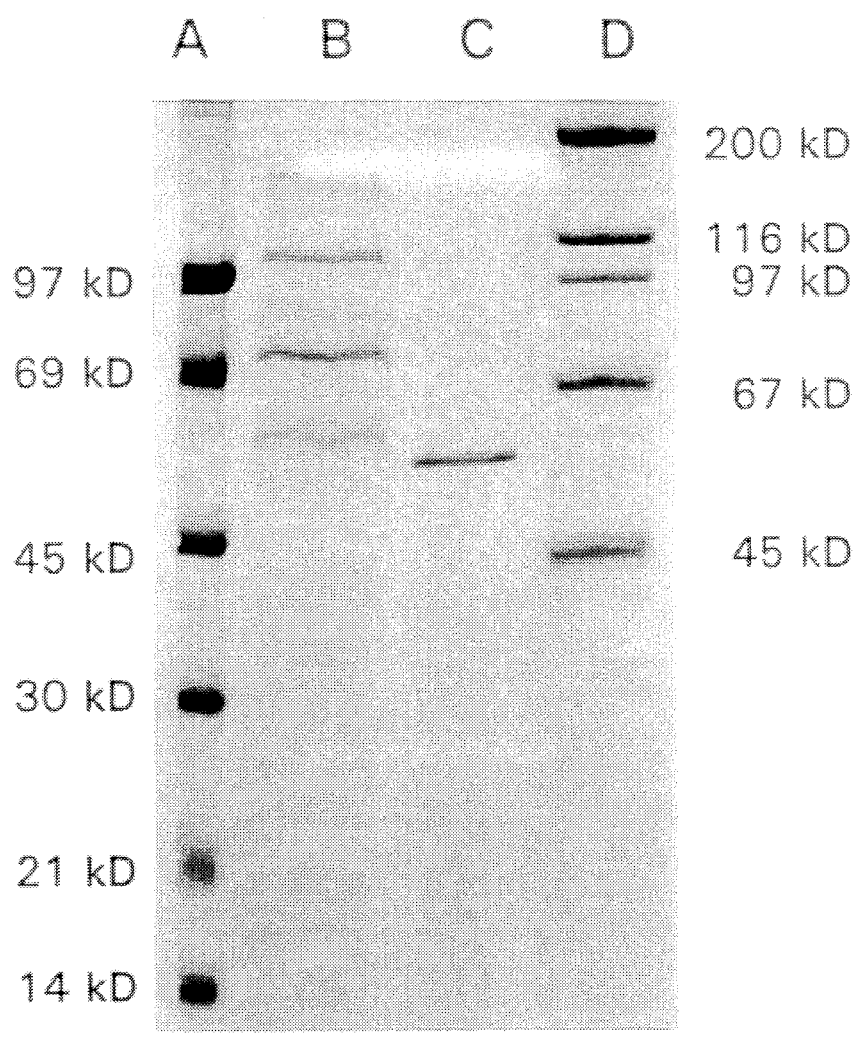

United States Patent [19]

Jacobs

[11] Patent Number: 5,612,042
[45] Date of Patent: Mar. 18, 1997

[54] **VACCINE AGAINST *STREPTOCOCCUS SUIS* INFECTION**

[75] Inventor: Antonius A. C. Jacobs, Kessel, Netherlands

[73] Assignee: Akzo Nobel NV, Arnhem, Netherlands

[21] Appl. No.: 242,406

[22] Filed: May 13, 1994

[30] Foreign Application Priority Data

May 17, 1993 [EP] European Pat. Off. .............. 93201401

[51] Int. Cl.$^6$ .................. A61K 39/085; A61K 39/00; A61K 39/385; A61K 39/09
[52] U.S. Cl. .................... 424/237.1; 424/184.1; 424/282.1; 424/185.1; 424/197.11; 424/825
[58] Field of Search ............... 424/237.1, 282.1, 424/184.1

[56] References Cited

U.S. PATENT DOCUMENTS 5,059,419  10/1991  Jacobs ........................ 424/87

OTHER PUBLICATIONS

Holt et al. 1990. Protective effect of sera raised against different . . . J. Comp. Path. 103:85–94.

Holt, M.E. et al., "Protective Effect of Sera Raised Against Different Fractions of Streptococcus Suis", *Journal of Comparative Pathology*, vol. 103, No. 1, Jul. 1990, pp. 85–94

Gottschalk et al., "Production and Characterization of Two Streptococcus Suis Capsular Type 2 Mutants", *Veterinary Microbiology*, vol. 30, No. 1, Jan., 1992, pp. 59–71.

Vecht, U. et al., "Identification of Two Proteins Associated with Virulence of Streptococcus Suis Type 2", *Infection and Immunity*, vol. 59, No. 9, Sep., 1991, pp. 3156–3162.

Jacobs et al. 1994. Identification purification and characterization of a Trial . . . Infect. & Immun. 62(5):1742–48.

Gottschalk et al. 1991. Characterization of six new capsular types (23 through 28) . . . J. Clin. Microbiol. 29(11):2590–94.

*Primary Examiner*—James C. Housel
*Assistant Examiner*—N. M. Minnifield
*Attorney, Agent, or Firm*—Mary E. Gormley; William M. Blackstone

[57] ABSTRACT

The present invention relates to a polypeptide of the bacterium *Streptococcus suis* with a molecular weight of about 54 kD, capable of inducing neutralising antibodies against *Streptococcus suis*. The invention also relates to a vaccine against *Streptococcus suis* infection, and a method for the preparation of such a vaccine.

11 Claims, 3 Drawing Sheets

VACCINE AGAINST *STREPTOCOCCUS SUIS* INFECTION

The present invention is concerned with a polypeptide of *Streptococcus suis*, a vaccine for the protection of pigs against diseases caused by *Streptococcus suis*, antibodies reactive with the *Streptococcus suis* polypeptide and a method for the preparation of such a vaccine.

*Streptococcus suis* has been identified as a major cause of contagious disease in pigs, which is characterised by arthritis, septicemia, meningitis, pericarditis, endocarditis, polyserositis and/or pneumonia (Clifton-Hadley, F. A.; Br. Vet. Journ. 139: 1–5 (1983), Vecht et al; Vet. Quarterly 7: 315–321 (1985), Windsor, R. S.; Vet rec. 101: 378–379 (1977), Higgins et al; Can. J. Vet. Res. 54: 170–173 (1990), Devriese et al; Vet. Rec. 127: 68 (1990))

Morbidity is especially high in piglets between 3–12 weeks of age (Windsor, R. S. and Elliot, S. D.; J. Hyg. Camb., 75: 69–78 (1975), Guise et al; Vet. Rec. 117: 43–44 (1985), Hoffman, L. J. and Henderson; L. M. Am. Assoc. Vet. Lab. Diagnosticians 28$^{th}$ Ann. Proc. 201–210 (1985)). Although swine of all ages are susceptible to this bacterial agent, mortality in swine over 14 weeks of age is low. (Guise et al; Vet. Rec. 117: 43–44 (1985), Hoffman, L. J. and Henderson; L. M. Am. Assoc. Vet. Lab. Diagnosticians 28$^{th}$ Ann. Proc.: 201–210 (1985)).

Occasionally, the organism is also associated with disease in other animal species and man (Devriese et al; Vet. Rec. 127: 68 (1990), Hommez et al; Vet. Rec. 123: 626–627 (1988), Arends et al; Rev. Infect. Dis 10: 131–137 (1988), Gottschalk et al; J. Clinic. Microbiol. 27: 2633–2636 (1989), Arends, J. P. and Zanen. H. C.; Rev. Infect. Dis 10: 131–137 (1988)). Infection in these cases usually occurs through skin lesions.

*S. suis* disease has first been described from the Netherlands by DeMoor (DeMoor, C. E.; Antonie van Leeuwenhoek 29: 272–280 (1963)). Since then, other researchers have reported outbreaks from other European countries as well as from Canada, the United States and Australia. (Sanford, E. and Tilker, M. E.; J. Am. Vet. Med. Assoc. 23: 5–97 (1982), Perch et al; J. Clin. Microbiol. 17: 993–996 (1983), Larson, D. J. and Kott, B.; Am. Assoc. Vet. Lab. Diagnosticians 28$^{th}$ Ann. Proc.: 121–130 (1985), Guise et al; Vet. Rec. 117: 43–44 (1985), Clifton-Hadley, F. A.; Br. Vet. Journ. 139: 1–5 (1983).

*Streptococcus suis* strains have been subdivided in a large number of different serotypes.

Serotype determination is based on the capsular polysaccharide antigen (Koehne et al; Am. J. Vet. Res. 40: 1640–1641 (1979), Perch et al; J. Clin. Microbiol. 17:993–996 (1983)).

So far, 29 different serotypes have been detected worldwide.

There is however a certain prevalence of several serotypes in distinctive countries. In Scandinavian countries, serotype 7 is most prevalent, whereas in Austria, serotype 9 is mostly found. The most prevalent serotype found worldwide is serotype 2 (Gogolewski et al; Aust. Vet. J. 67: 202–204 (1987), Boetner et al; Acta Path. Microbiol. Immunol. Scand. Sect. B 95: 233–239 (1987)).

Little is known about pathogenesis, virulence factors or protective antigens of *Streptococcus suis*.

This implicates that there is no lead to which factors are needed for efficient vaccination against the pathogen.

One commonly followed route to make a vaccine against a bacterial disease, is the production and testing of a whole cell vaccine preparation.

This has also been done for *Streptococcus suis* and it appeared that whole cell vaccines do produce significant protection in pigs against homologous challenge (Holt et al; Res. Vet. Sci. 48:23–27 (1990)).

It seems likely however (Kebede et al; Vet. Microbiol. 22: 249–257 (1990)), that protection obtained with whole cell preparations is serotype-specific. Other general and well-known disadvantages of whole cell vaccines are a) unwanted reactions at and around the site of injection, and b) the large amount of non-specific protein that is administered, compared to the amount of material actually responsible for the induction of protection.

Given the fact that at this moment on the basis of polysaccharide capsule already 29 different *Streptococcus suis* serotypes are known, this implicates that whole cell based vaccines should contain many serotypes to obtain broad protection.

Such a vaccine has indeed been made to protect humans against pneumonia, caused by *Streptococcus pneumonia* (Boulnois, G. J.; Journ. Gen. Microbiol. 138: 249–259 (1992)).

This vaccine contains 23 polysaccharides from the most frequently encountered serotypes. This vaccine has, apart from its complexity, significant shortcomings, due to the low degree of immunogenicity of capsular polysaccharides.

Therefore, many attempts have been made to determine the distinctive factors that possibly play a role in the pathogenesis of *Streptococcus suis*.

Haemagglutinins and fimbriae as potential virulence factors have been described, but their precise role or function in pathogenesis is not known and the respective molecules or proteins have not been identified. (Jacques et al; J. Bacteriol. 172: 2833–2838 (1990), Gottschalk et al; J. Clin. Microbiol. 28: 2156–2158 (1990 )).

So far, four proteins have been proposed as potential virulence factors:

a) a 44 kD protein (Gottschalk et al; Vet. Microb. 30: 59–71 (1992))

b) a 94 kD protein (Holt et al; J. Comp. Path. 1003: 85–94 (1990))

c) a 110 kD protein (the E(xtracellular) F(actor)) (Vecht et al; Infect. Immun. 59: 3156–3162 (1991), Vecht et al; Infect. Immun. 60: 550–556 (1992), Smith and Vecht; PCT-Application WO 92/16630).

d) a 136 kD protein (the M(uraminidase) R(eleased) P(rotein) (Vecht et al; Infect. Immun. 59: 3156–3162 (1991), Vecht et al; Infect. Immun. 60: 550–556 (1992), Smith and Vecht; PCT-Application WO 92/16630). The 44 kD protein was found in pathogenic strains of *S. suis* serotype 2 and appeared to be absent in a non-pathogenic mutant strain. Antisera raised against a mutant strain lacking the 44 kD protein was not sufficient to obtain full protection against the parent strain. It therefore is supposed to be involved in virulence.

Antiserum, raised in rabbits against the 94 kD protein of *S. suis* serotype 2 has been shown to induce protection in mice against homologous challenge.

The 110 kD and 136 kD proteins appear to be present in highly pathogenic strains and absent in non-pathogenic strains, whereas the 110 kD protein appears to be absent in strains with low pathogenicity.

This may indicate that the 110 kD and 136 kD proteins are involved in pathogenesis. On the other hand, so far no protection experiments on the basis of isolates of these proteins have been published.

In conclusion: of all potential virulence factors determined so far, only the 44 kD and 94 kD protein have been shown to play a role in protection against serotype 2. This protection has only been demonstrated in mice, and with a homologous challenge.

In addition to this, so far the presence of the four proteins mentioned above has only been shown in *Streptococcus suis* serotype 2 strains.

As mentioned above, given the large number of different serotypes, a serotype-independent and serologically cross-reactive protective antigen would be a clearly preferred basis for a vaccine. Such an antigen has not been described for *Streptococcus suis*.

It has been surprisingly found now, that some strains of *Streptococcus suis* excrete a polypeptide having a molecular weight of about 54 kD, that can be activated by thiol, can be inhibited by cholesterol and shows haemolytic activity.

The haemolytic toxins all share the phenomenon of damaging mammalian cell by disrupting membrane integrity and/or function. This disruption is probably due to pore structure formation by oligomeric forms of the toxin, once incorporated into the cell membrane.

It was shown, that the haemolytic polypeptide of the present invention is a thiol-activated toxin. Thiol-activated toxins are only active in the reduced state and reversibly lose activity on oxidation (Smyth, C. J. and Duncan, J. L.; Bacterial Toxins and Cell Membranes Jeljaszewicz, J. and Wadstrom, T (eds.) London, Academic Press: 129–183 (1978)).

Although the role of the thiol-group is far from clear, it is supposed to be an important part of a sequence motif that is essential for the generation of lesions in membranes.

The mechanism behind cytolytic action of a certain group of haemolysins supposes binding of the haemolytic polypeptide to cholesterol in the mammalian cell membrane. Once the protein has attached to the cell, it enters the lipid bilayer. Then, oligomeric haemolysin complexes are formed, that are supposed to form transmembrane pores.

It was demonstrated that the haemolytic activity of the polypeptide of the present invention belongs to the group of haemolysins that can be inhibited by cholesterol. Cholesterol appears to play a key role in the binding of the haemolysin to susceptible cells. Several models have been proposed in which cholesterol is the primary binding site of the toxin to the cell. Free cholesterol is a potent inhibitor of cytolytic activity, which may be explained by the fact that if the sterol-binding site on the toxin is occupied by (free) cholesterol, it can no longer bind to (membrane bound) cholesterol. (Boulnois et al; Mol. Microbiol. 5: 2611–2616 (1991)).

The haemolytic polypeptide of the present invention has an estimated molecular weight of about 54 kD. This molecular weight was determined according to standardized methods using polyacrylamide gel-electrophoresis as described in Example II. Lane C in FIG. 1 shows the purified polypeptide flanked by marker molecules (lanes A and D).

The haemolytic polypeptide of one strain of *Streptococcus suis*; strain P1/7, has further been characterised by the determination of its N-terminal amino acid sequence. SEQ ID NO: 1: represents the N-terminal sequence of the polypeptide. Haemolytic polypeptides can be isolated from some but not all *Streptococcus suis* strains. There may be slight modifications in the nucleic acid sequence of the gene coding for the haemolytic polypeptide in the respective haemolytic peptide producing *S. suis* strains. These modifications may have no effect on the amino acid sequence of the polypeptide, in case that the modification is such that the new triplet codes for the same amino acid. This is e.g. the case when the G in the triplet CTG, coding for Leucine, is replaced by a C, also coding for Leucine. If however the T would have been replaced by a C, the newly formed triplet codes for Proline instead of Leucine. This would lead to variation in the amino acid sequence of the haemolytic polypeptide.

Variation in amino acid sequence may be the result of replacement of one or more amino acids by functional equivalents, or, more seldom, of the introduction of a STOP-codon or, in case of deletions/insertions in the nucleic acid sequence, insertion or deletion of one or more amino acids. Replacement by functionally equivalents is often seen. Examples described by Neurath et al (The Proteins, Academic Press, New York (1979), page 14, FIG. 6) are i.a. the replacement of the amino acid alanine by serine; Ala/Ser, or Val/Ile, Asp/Glu, etc. In addition to the variations leading to replacement by functional equivalent amino acids mentioned above, variations may be found, in which an amino acid has been replaced by another amino acid that is not a functional equivalent. This kind of variation only differs from replacement with functional equivalents in that it may yield a protein that has a slight modification in its spatial folding.

It goes without saying, that variations in the nucleic acid sequence coding for the haemolytic polypeptide, leading to variations in the amino acid sequence of the haemolytic polypeptide in such a way that the immunogenic activity of the polypeptide is retained, are also within the scope of the present invention.

The invention also relates to a vaccine capable of protecting pigs against *Streptococcus suis* infection, comprising the haemolytic polypeptide mentioned above, or a portion thereof capable of inducing an immune response against the haemolytic polypeptide of *S. suis*. Such a vaccine can be made e.g. by using a synthetic polypeptide mimicking the polypeptide of the present invention or a portion thereof that is capable of inducing an immune response against the haemolytic polypeptide of *S. suis*.

Another way of making such a vaccine is biochemical purification of the haemolytic polypeptide from a bacterial culture. This can e.g. be done by centrifugation of the bacteria, and the use of gel-filtration columns for separation of the haemolytic polypeptide from other components. Further purification may e.g. be done by selective precipitation in ammonium-sulphate, followed by centrifugation and dissolving the pellet in a suitable buffer.

Such a vaccine can also be made e.g. by molecular cloning techniques. With these techniques, the nucleic acid sequence coding for the polypeptide of the present invention or a portion thereof that is capable of inducing an immune response against the haemolytic polypeptide of *S. suis*, can be cloned in an expression vector, and subsequently be expressed in a suitable expression system. The expression product can then be used in a vaccine. Possible expression systems are bacterial, yeast, fungal, insect and mammalian cell expression systems.

Another way of making the polypeptide is the cloning of the genetic information for the polypeptide into a suitable virus vector, and to use the host cell of the virus for the expression of the protein. Such systems are e.g. the vaccinia virus vector in combination with susceptible mammalian cells, or the baculo virus vector with *Spodoptera frugiperda* cells. Crude or purified cell lysates comprising the expressed polypeptide can then be used as a vaccine basis.

Still another approach is to use viruses having the pig as a host animal as a so-called Live Recombinant Carrier virus. This LRC is a virus, in which additional genetic information has been cloned. Animals infected with this recombinant virus will produce an immunogenic response not only against the immunogens of the vector virus, but also against the immunogenic parts of the polypeptide(s) for which the genetic code is additionally cloned into the recombinant virus.

A virus that is particularly useful as a Live Recombinant Carrier virus for carrying genetic information from foreign pig pathogenic organisms is the Pseudorabies virus. This virus has been used before successfully as a LRC for e.g. combined Pseudorabies/Hog Cholera Virus vaccination.

In a preferred form, the vaccine according to the present invention also comprises other *Streptococcus suis* immunogens.

It has been found, that antisera raised against the *S. suis* serotype 2 haemolytic polypeptide are reactive with haemolysins of all other haemolysin-producing *S. suis* strains, regardless their serotype.

This has not been demonstrated with the 44 kD, 94 kD, 110 and 136 kD *Streptococcus suis* polypeptides mentioned above.

Nevertheless, a vaccine according to the present invention and additionally containing one of these, or any other *Streptococcus suis* immunogens has an even better efficiency. This higher efficiency may be e.g. the result of a synergistic effect. This can lead to the production of more efficient vaccines with an even lower antigenic load.

In a more preferred form, the vaccine according to the present invention also comprises a carrier coupled to the polypeptide of the present invention. As carriers, other molecules such as Keyhole Limpet Haemocyanine, Bovine Serum Albumin, but also complex sugar molecules can be used.

In an even more preferred form, the vaccine according to the present invention comprises a capsular polysaccharide coupled to the polypeptide of the present invention.

Methods for covalent linkage of polypeptides to carbohydrates have been described i.a. by Dick, W. E. and Beurt, M.; Contrib. Microbiol. Immunol. 10: 48–114 (1989).

It is clear, that other carrier types or other methods of linkage of a polypeptide to a carbohydrate are also within the scope of the present invention.

In a further embodiment, the vaccine according to the present invention also comprises antigens from other pig-pathogenic organisms and viruses. Such organisms and viruses are e.g. *Actinobacillus pleuropneumoniae*, Pseudorabies virus, Porcine Influenza virus, Porcine Parvovirus, Transmissible Gastroenteritisvirus, rotavirus, *Escherichia coli, Erysipelothrix rhusiopathiae, Pasteurella multocida* and *Bordetella bronchiseptica.*

The vaccine according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers, muramyldipeptides, Quill A$^{(R)}$, mineral oil e.g. Bayol$^{(R)}$ or Markol$^{(R)}$, vegetable oil, and Carbopol$^{(R)}$ (a homopolymer), or Diluvac$^{(R)}$ Forte.

The vaccine may also comprise a so-called "vehicle". A vehicle is a compound to which the polypeptide adheres, without being covalently bound to it. Often used vehicle compounds are e.g. aluminium hydroxide, -phosphate or-oxide, silica, Kaolin, and Bentonite.

A special form of such a vehicle, in which the antigen is partially embedded in the vehicle, is the so-called ISCOM (EP 109,942, EP 180.564, EP 242,380)

In addition, the vaccine may comprise one or more suitable surface-active compounds or emulsifiers, e.g. Span or Tween.

Often, the vaccine is mixed with stabilisers, e.g. to protect degradation-prone polypeptides from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

It goes without saying, that other ways of adjuvating, adding vehicle compounds or diluents, emulsifying or stabilizing a polypeptide are also embodied in the present invention.

In another embodiment, antibodies monospecifically reactive with the polypeptide of the present invention or an antigenic portion thereof are used to confer passive immunity.

Monospecific antibodies are antibodies that are specifically capable of reacting with the 54 kD polypeptide of the present invention, or a portion thereof, without being specifically reactive with other *Streptococcus suis* antigens.

Antibodies against pathogens can successfully be used in passive immunization. The advantage of this kind of therapy is, that antibodies are available for application at the moment the infection hits. Thus no time is lost in waiting for the immune system of the host to be activated and to develop a sufficiently high defense level. Especially in the case that infection has already occurred, and the disease is in progress, application of antibodies instantaneously cures the animal from pathogens and toxins produced by the pathogen. A vaccine capable of protecting pigs against disease after infection with *Streptococcus suis* on the basis of antibodies against *S. suis* haemolytic polypeptide is thus also embodied in the present invention.

The present invention also provides a method for the preparation of a vaccine capable of protecting mammals against infection by *streptococcus suis* comprising mixing the polypeptide according to the present invention with a pharmaceutically acceptable carrier, adjuvant or diluent.

EXAMPLE I

Bacterial Strains

*S. suis* type 2 strains P1/7 and 688/9 were provided by Dr. T. Alexander, University of Cambridge, U.K. Type 2 strains 4005, D282, 3921, 3977, 3889 and T15 were obtained from Dr. U. Vecht, CDI-DLO, Lelystad, the Netherlands. Type 7 strains 10681, 10727 and 14391 were provided by Dr. B. Nielsen, Intervet Scandinavia, Copenhagen, Denmark. Reference strains 1–22 were obtained from Dr. J. Henrichsen, Statens Serum Institute, Copenhagen, Denmark.

Strain B10, serotype 1, is a recent field isolate obtained from the "Gezondheidsdient voor dieren, OostNederland", at Deventer, The Netherlands.

Strains NV92109 serotype 8, 22089KM serotype 9, and 220891GV serotype 14 are recent field isolates from diseased pigs.

Bacterial Cultures

Bacterial strains were streaked out on sheep blood agar and cultured for 24 hours at 37° C. For the determination of haemolysin production in batch cultures, a few colonies were inoculated in 100 ml Todd Hewitt broth (Difco) and cultured at 37° C., until the end of the exponential growth phase (usually 5–6 hours). Subsequently, the cells were removed by centrifugation at 10,000 xg for 10 min., and the supernatant stored at −20° C., until use.

Haemolysin inhibition test

For the titration of the haemolysin inhibition titer of sera, serial two-fold dilutions (75 μl) of test sera were prepared in deep-well titer plates using 10 mM Tris buffered saline pH 7,4 as diluent. Subsequently, 75 μl of a haemolysin solution containing $2^5$ haemolytic units was added to each well. After incubation at 20° C., for 10 min., 150 μl of a 2% (washed) horse erythrocytes suspension was added to each well and the test was completed as described above for the titration of haemolytic activity. The titer was defined as the highest dilution resulting in minimally 50% inhibition of haemolysis. The capacity of specific pig serum P399 to purified haemolysin (derived from *S. suis* type 2) to inhibit haemolytic activity produced by different (serotype) strains was tested in a single well using 75 μl 1:128 pre-diluted serum P399 and 75 μl undiluted culture supernatants of the different strains. The test was then completed as described above. Pre-immune serum, also pre-diluted 1:128, was used as control (maximal haemolysis). Cross-neutralisation was apparent if serum P399 inhibited haemolysis by more than 50% compared to the pre-immune serum. Samples with a haemolysin titer $<2^4$ give no results in this test because the maximal haemolysis (pre-immune serum) does not reach two times the background (serum P399).

EXAMPLE II

Figure 2:
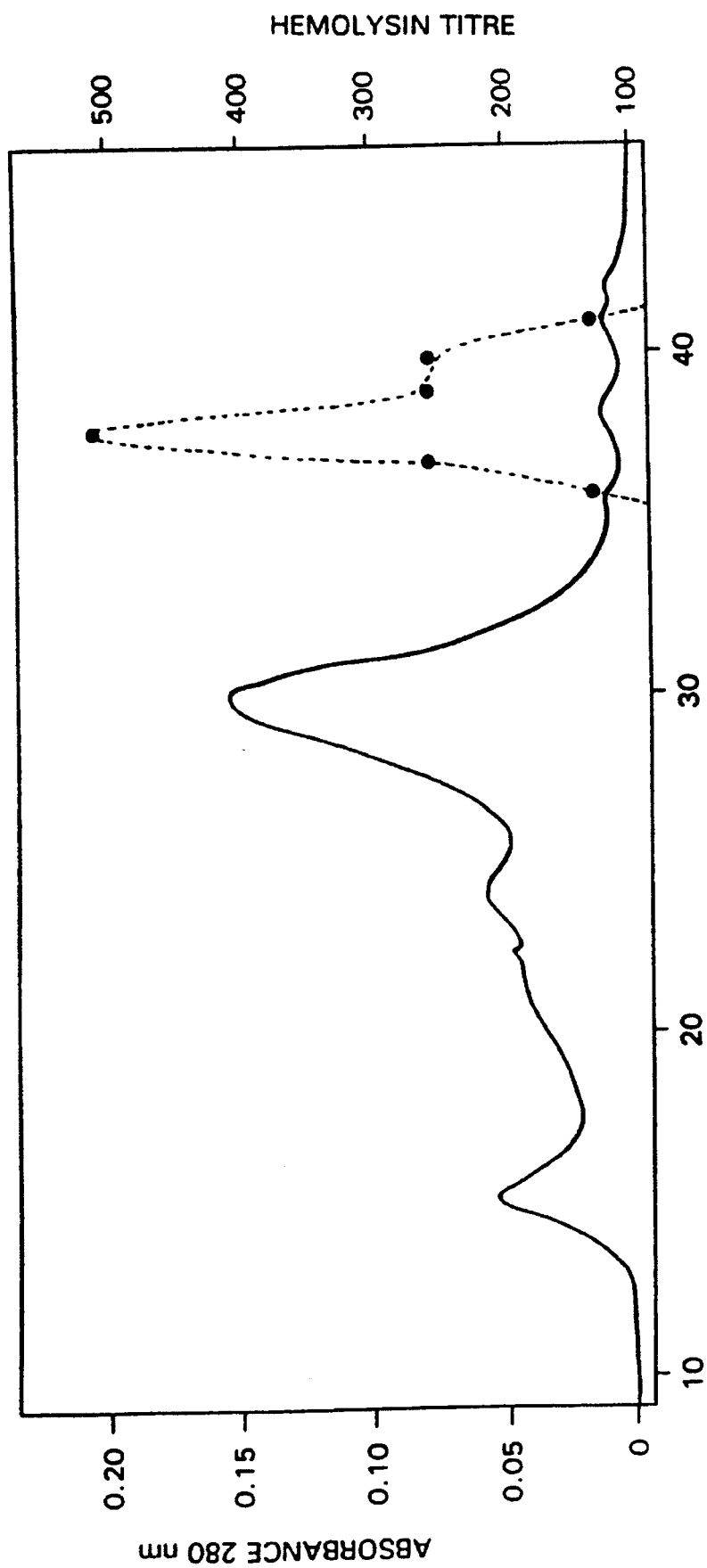

Purification of Haemolysin 250 ml of an overnight culture of strain P1/7 was grown in anaerobic conditions for 6 hours in 12 litres of Todd Hewitt broth at 37° C., after which the cells were removed by continuous flow centrifugation. The culture supernatant was cooled to 4° C., passed through a 0.8 μm filter and then concentrated to 150 ml on PTCG 10,000 NMWL filters. After passing a 0.2 μm filter, 1.0 ml portions were applied on a Superose-12 gel filtration column (FPLC, Pharmacia), and eluted in 40 mM phosphate buffered saline pH 7,2 containing 0.5 M NaCl. 0.5 ml fractions were collected and analysed in SDS-PAGE, immunoblotting and in the haemolysin test. Haemolytic peak activity eluted in fractions 35–45 (FIG. 2).

Figure 3:
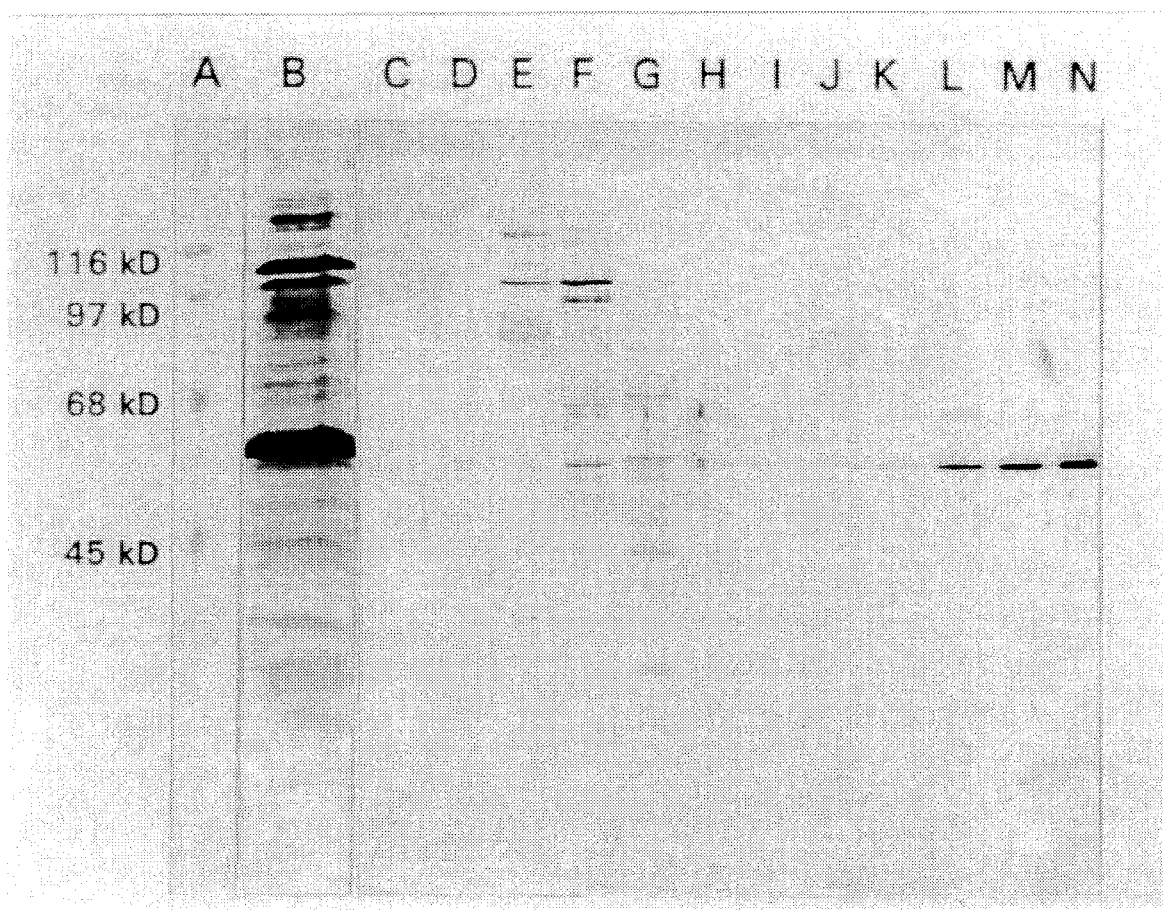

Analysis of the different column fractions on SDS-PAGE and immuno-blotting showed that the haemolytic activity had co-migrated with a single antigen at about 54 kD (FIG. 3). Haemolytic fractions 35–45 were pooled, and minor contaminants were removed by selective precipitation with 50% $(NH_4)_2SO_4$ at 4° C., for 3 hours. After centrifugation, the pellet was resuspended in 20 ml 40 mM phosphate buffered saline pH 7.2. This final preparation appeared as a single polypeptide species at about 54 kD in SDS-PAGE after staining with Coomassie brilliant blue (FIG. 1), and had a specific activity of about $0.7 \times 10^6$ haemolytic units/mg after reduction with β-mercaptoethanol.

Protein Determination

Protein concentrations were measured by the method of Lowry et al. (Lowry et al; J. Biol. Chem. 193:265–275 (1951)) using bovine serum albumin as the standard.

SDS-PAGE and Western Blotting

SDS-PAGE in 9% slab gels and sample preparation were done essentially as described by Laemmli (Laemmli, U. K.; Nature 227: 680–685 (1970)). After electrophoresis, polypeptides were stained with Coomassie brilliant blue R250 or electro-blotted onto Immobilon PVDF membrane. Blots were probed with polyclonal rabbit serum R2089 or polyclonal mouse serum M189 (see section antisera). After washing, bound antibodies were visualized using horseradish peroxidase-goat-anti-rabbit or goat-anti-mouse conjugate, respectively, and Di-Amino Benzidine as the substrate.

Haemolytic Activity After Different Treatments

For all treatments 0.5 ml portions of purified Haemolysin in 40 mM phosphate buffered saline pH 7,2 with a titer of $2^7$ was used.

The effect of different temperature was measured in the haemolysin assay after incubation of the haemolysin at the respective temperatures i.e. −20° C., 4° C., 20° C., 37° C., and 100° C. To test the effect of proteinase-K treatment, 5 μl of a concentrated enzyme solution (2 mg/ml), was added to 0.5 ml of haemolysin solution and incubated for 10 min. at 20° C. Subsequently, any residual haemolytic activity was measured in the haemolysin assay.

To test the effect of reduction by β-mercaptoethanol, 5 μl of a 10% (v/v) β-mercaptoethanol solution was added to 0.5 ml of haemolysin solution and incubated for 10 min. at 20° C., after which the activity was measured in the haemolysin assay.

To test the effect of oxidation by $H_2O_2$ 5 μl of a 10% $H_2O_2$ solution was added to 0.5 ml of haemolysin solution followed by incubation at 20° C., for 10 min. Subsequently any residual activity was measured in the haemolysin assay.

The effect of alkylation of any thiol groups with TLCK (N-Á-p-tosyl-L-lysine chloromethylketone, Sigma) was determined by the addition of 5 μl of a 10% (w/v) TLCK solution to 0.5 ml of haemolysin solution followed by incubation at 20° C., for 10 min. Subsequently any residual activity was measured in the haemolysin assay.

The effect of cholesterol was tested by the addition of 10 μl of 5% cholesterol (in 10% ethanol) to 0.5 ml of haemolysin solution followed by incubation at 20° C., for 10 min., after which any residual activity was measured in the haemolysin assay.

The reversibility by reduction of some treatments was tested by the addition of excess β-mercaptoethanol (2% final concentration) to part of the reaction mixtures, followed by incubation at 20° C., for 10 min., and titration of haemolytic activity.

The effects of different treatments on haemolytic activity are shown in Table 1. The results show that the haemolysin is heat labile, and susceptible to proteinase-K digestion, oxidation by $H_2O_2$ and alkylation with TLCK. Furthermore, haemolytic activity is inhibited by cholesterol. After incubation with β-mercaptoethanol an increased activity was found and addition of excess β-mercaptoethanol to the $H_2O_2$-oxidized preparation resulted in the restoration of haemolytic activity. The addition of excess β-mercaptoethanol to the TLCK treated preparation resulted in a partial restoration of haemolytic activity. This partial restoration might be explained by the presence of oxidized thiol groups which had not reacted with TLCK. The effects of temperature and cholesterol could not be reversed by the addition of β-mercaptoethanol.

Duplicate samples in which the respective reagents were left out or in which the haemolysin was left out showed no effects of the respective methods on haemolytic activity or effects of reagents on erythrocytes, respectively.

Susceptibility of Different Species of Erythrocytes to Haemolysin

The susceptibility of different species of erythrocytes i.e. human, bovine, turkey, pigeon, mouse, chicken, guinea pig, rabbit, cat, dog and pig, was tested using a reduced (0.1% β-mercaptoethanol) preparation of purified haemolysin with a titer of $2^8$. Tests were carried out essentially as under: "Titration of haemolytic activity". All erythrocytes appeared about equally susceptible to the haemolysin. The titers varied from $2^7$ (mouse, cat and turkey) to $2^{10}$ (human).

N-terminal Amino Acid Sequence

The first 16 amino acid residues of purified haemolysin obtained from strain P1/7 were determined by automated Edman degradation as listed in SEQ ID NO: 1:.

Prevalence of Haemolysin Molecules in Different S. suis Strains

All strains available, including serotype strains 1–22, were cultured in Todd Hewitt broth until the end of the exponential growth phase (5–6 hours), after which the cells were removed by centrifugation. The presence of haemolysin molecules in the culture supernatant was determined in the haemolysin assay and by immunoblotting. Many but not all strains appeared to produce various amounts of haemolytic activity in the culture supernatant (Table 2).

All haemolytic samples including samples with low activity, appeared to be inhibited by cholesterol and $H_2O_2$. Furthermore, the addition of excess β-mercaptoethanol to the $H_2O_2$-oxidized preparations resulted in a complete restoration of haemolytic activity.

In summary, most strains tested appear to produce haemolytic activity in the culture supernatant which is immunologically and biochemically related to haemolysin and no indications for other non-related haemolysins were found.

EXAMPLE III

Vaccines

Four vaccines based on purified haemolysin, concentrated culture supernatant or pooled Superose-12 column fractions 19–31, and placebo vaccine were prepared from strain P1/7.

For comparison, a vaccine based on purified EF was made. One vaccine based on concentrated culture supernatant was prepared from strain B10.

The vaccines were prepared as follows:

Purified haemolysin (40 µg protein/ml) was 1:1 mixed with Diluvac Forte® adjuvant until a homogeneous microemulsion was obtained. This vaccine was termed VAC-SLY.

For the vaccine containing concentrated culture supernatant, part of the PTCG concentrate (1.9 mg protein/ml) was 1:1 mixed with Diluvac Forte® adjuvant until a homogeneous suspension was obtained. This vaccine was termed VAC-CCS.

The third vaccine was prepared by mixing (1:1) the pooled and concentrated superose-12 column fractions 19–31 (containing 2 mg protein/ml), with Diluvac Forte® adjuvant until a homogeneous suspension was obtained. Column fractions 19–31 contained most of the extracellularly produced proteins of S. suis strain P1/7, but was essentially free from haemolysin. This vaccine was termed VAC-SCF.

A fourth vaccine was prepared by filtration of culture supernatant over a 0.2µ filter followed by precipitation with 60% saturated $(NH_4)_2SO_4$ for 16 hrs at 0° C. After centrifugation, the pellet was resuspended in PBS as to give a preparation that is about 100-fold concentrated compared to the culture supernatant.

Placebo vaccine was prepared as described above except that the antigen solution was replaced by 40 mM phosphate buffered saline pH 7,2.

Strain B10 was used to prepare a vaccine based on precipitation with 60% saturated $(NH_4)_2SO_4$ for 16 hrs at 0° C., as was described above The EF-vaccine was obtained after hydrophobic interaction chromatography (Phenyl Sepharose phast flow column, high substituted) of strain P1/7 culture supernatant, using a decreasing gradient of $(NH_4)_2SO_4$. The final purified EF preparation (after dialysis and dilution) contained about 150 µg of EF/ml. Based on SDS-PAGE and Coomassie staining, the preparation had >95% purity.

Antiserum

Specific polyclonal pig serum (P399) to purified haemolysin was obtained as follows. A 4 weeks old pig was immunized intramuscularly (neck) with 2 ml of vaccine VAC-SLY. Two weeks after the priming the pig was boosted using the same (amount of) vaccine and vaccination route. Two weeks after the booster the pig was bled and the serum stored at −20° C., until use.

Mouse Protection Test

Four weeks old Balb-C mice were divided into 4 groups and vaccinated subcutaneously with 0.5 ml of VAC-CCS, VAC-SCF, VAC-SLY or with placebo vaccine. Two weeks after priming the mice were boosted using the same vaccines and vaccination route. Two weeks after the booster the mice were challenged intraperitoneally (0.5 ml) using a 6 hours culture of strain P1/7 in Todd Hewitt broth containing $4 \times 10^9$ CFU/ml. After challenge, mortality was recorded for 7 days.

Results

After the challenge, placebo vaccinated mice died within 3 days, whereas mice vaccinated with VAC-CCS and VAC-SLY appeared completely protected (Table 3). VAC-SCF induced only partial protection. This vaccine contained most of the extracellularly produced antigens of strain P1/7, but was essentially free from haemolysin.

Conclusion

Therefore we conclude that a vaccine containing purified haemolysin according to the present invention is protective in mice. This indicates that the haemolysin is a virulence factor and that the neutralisation of this single virulence factor is sufficient to protect mice against the detrimental effects of a S. suis type 2 infection.

Mouse Heterologous Protection Experiment

Experimental Animals

BALB/c mice (4 weeks old) obtained from Iffa Credo were used.

Experimental Set Up

Groups of 30 mice (2×15) were vaccinated, once, subcutaneously with 0.4 ml of the respective vaccines or left unvaccinated (one group of 30 mice) as indicated in table 6. Four weeks after vaccination half of the mice per group were challenged intraperitoneally with 0.5 ml of a six hours culture of strain B10 (type 1) and the other half with strain P1/7 (type 2).

Mortality was recorded during 7 days. Strain B10 has a lower pathogenicity for mice (about 20% mortality) as compared to strain P1/7 (100% mortality). Therefore, with the B10 challenge groups the number of diseased mice was recorded as well. Just before challenge bloodsamples were taken and pooled group sera tested in an immunoblot.

Results

In the hemolysin test culture supernatant of strain B10 (serotype 1) had a hemolytic activity of $2^{9.5}$, whereas culture supernatant of strain P1/7 (serotype 2) had an activity of $2^7$. Thus strain B10 produced about 5x more hemolytic activity as compared to strain P1/7.

Based on SDS-PAGE and Coomassie staining it appeared that both concentrated culture supernatants of strain B10 and P1/7 contained a 54 kD protein (SLY) and that concentrated culture supernatant of strain B10 contained more of the 54 kD protein which is in accordance with the higher activity.

Purified EF contained no 54 kD protein.

After challenge it turned out that both culture-supernatant-containing vaccines induced homologous as well as heterologous protection in mice (see table 6). When pooled group sera were tested in an immunoblot using culture supernatant of strain P1/7 or B10 as antigen it appeared that both culture supernatant vaccines had induced anti-SLY antibodies (Table 6). With anti-B10-culture-supernatant a stronger reaction was found as compared to anti-P1/7-culture-supernatant. When tested heterologously in an immunoblot (anti-B10-culture-supernatant against P1/7 culture supernatant and anti-P1/7-culture-supernatant against B10 culture supernatant) the 54 kD antigen was the major or the only reactive antigen.

Mice vaccinated with purified EF although given in high doses, appeared not protected against homologous or heterologous challenge, although antibodies were induced (table 6).

Conclusion

Both culture supernatant vaccines induced homologous as well as heterologous protection in mice. The fact that the 54 kD antigen is the only or the major reactive antigen in an immunoblot when tested heterologously, clearly shows that SLY is a cross protection factor in mice.

Pig Protection Experiment

VAC-SLY, VAC-SCF and PLACEBO were prepared as described above.

VAC-SLY contained 20 μg/ml of purified haemolysin in Diluvac Forte$^{(R)}$ adjuvant. VAC-SCF (2 mg protein/ml) contained most of the extracellularly produced proteins of Streptococcus suis in Diluvac Forte® adjuvant, but was essentially free from haemolysin.

Nine 4 weeks old pigs were divided into 3 groups of 3 pigs each and vaccinated (intramuscularly, neck) with 2 ml of VAC-SLY, VAC-SCF or PLACEBO. Two weeks after priming the pigs were boosted using the same vaccines and vaccination route. Two weeks after the booster the pigs were challenged intravenously (0.5 ml) using a 6 hours culture of strain P1/7 in Todd Hewitt broth, containing $4 \times 10^9$ CFU/ml. Just before priming and challenge blood samples were taken and the sera stored at $-20°$ C., until use.

Bacterial Reisolation

At necropsy swabs were taken from the brain, lung and tarsus if possible from the most affected area. Bacterial growth was scored 0, 1, 2, 3 or 4 based upon the dimension in which growth occurred.

Results

After the challenge the PLACEBO vaccinated pigs developed severe clinical signs, characterized by limping involving several joints, depressed appearance and high temperatures. Two of three PLACEBO vaccinated pigs developed neurological signs and were so badly affected that they had to be euthanized. The VAC-SCF vaccinated pigs showed the same clinical signs as the controls but to a lesser extent. One pig of this group developed neurological signs and had to be euthanized. The VAC-SLY vaccinated pigs were the least affected. The pigs of this group showed only mild signs which subsided more quickly as compared to both other groups. The clinical results are summarized in Table 4. Total clinical score is the sum of the scores for the various clinical signs. At dissection, the PLACEBO vaccinated pigs appeared to have severe polyarthritis with most joints affected (Table 5). The VAC-SCF vaccinated pigs had also polyarthritis but to a lesser extent, whereas most joints of the VAC-SLY vaccinated pigs appeared normal (Table 5).

Streptococcus suis was reisolated in different amounts and from different tissues of 2 of 3 PLACEBO vaccinated pigs and from all 3 VAC-SCF vaccinated pigs but not from the VAC-SLY vaccinated pigs (the numbers under "reisolation total score" represent the relative amount of bacteria, reisolated from the total amount of animals in each group) (Table 5).

Histological examination of brain samples (Table 5) revealed meningitis for two VAC-SCF vaccinated pigs and two PLACEBO vaccinated pigs.

Conclusion

Although pigs vaccinated with VAC-SLY showed clinical signs during a few days, these signs were significantly less severe and of shorter duration compared to VAC-SCF or PLACEBO vaccinated pigs. At dissection fibrinous arthritis was less severe and less frequently observed in the VAC-SLY vaccinated pigs compared to the VAC-SCF or PLACEBO vaccinated pigs. In addition, 2 SCF vaccinated pigs and 2 PLACEBO vaccinated pigs had meningitis, whereas none of the VAC-SLY vaccinated pigs had meningitis. Moreover, the lungs, joints and brains of the VAC-SLY vaccinated pigs appeared sterile whereas from most of these organs of both other groups, Streptococcus suis type 2 was reisolated. In an immunoblot, sera of the VAC-SLY vaccinated pigs (taken at day of challenge) reacted with a single antigen band at 54 kD, in whole culture supernatant, confirming that haemolysin was immunogenic and that the haemolysin preparation was highly purified.

The results indicate that Streptococcus suis haemolysin is an important factor and that the neutralization of this single factor is sufficient to protect pigs significantly against the detrimental effects of a Streptococcus suis infection, and to clear the bacteria from the different organs/tissues.

TABLE 1 activity of purified haemolysin after various treatments

| Treatment | Treatment time | 2log hemolysin titre | 2log hemolysin titre after addition of 2% β-mercaptoethanol |
| --- | --- | --- | --- |
| $-20°$ C. | 7 days | 7 | ND$^a$ |
| $4°$ C. | 7 days | 6 | ND |
| $20°$ C. | 7 days | 3 | ND |
| $37°$ C. | 7 days | 0 | 0 |
| $100°$ C. | 5 min. | 0 | 0 |
| $20°$ C. | 10 min. | 7 | ND |
| proteinase-K (20 μg/ml) | 10 min., $20°$ C. | 0 | ND |
| β-mercaptoethanol (0.1%) | 10 min., $20°$ C. | 12 | ND |
| $H_2O_2$ (0.1%) | 10 min., $20°$ C. | 0 | 12 |
| TLCK (0.1%) | 10 min., $20°$ C. | 2 | 6 |
| Cholesterol (0.1%) | 10 min., $20°$ C. | 0 | 0 |

$^a$ND = not determined

TABLE 2

Prevalence of haemolysin like molecules in culture supernatants of different *S. suis* strains.

| strain | serotype | reference strain (R) | phenotype[a] | 2log hemolysin titre[b] | inhibition of hemolysin by 0.1% cholest.[b] | reversible inactivation by ox/red.[b] | inhibition of hemolysin by serum P399[b] | presence of 54 kD in immunoblot[b] |
|---|---|---|---|---|---|---|---|---|
| S428 | 1 | R |  | 5 | + | + | + | + |
| RS 2651 | 1/2 | R |  | 6 | + | + | + | + |
| R735 | 2 | R | MRP+EF− | 5 | + | + | + | + |
| P1/7 | 2 |  | MRP+EF+ | 8 | + | + | + | + |
| 688/9 | 2 |  | MRP+EF+ | 6 | + | + | + | + |
| 4005 | 2 |  | MRP+EF+ | 5 | + | + | + | + |
| D282 | 2 |  | MRP+EF+ | 7 | + | + | + | + |
| 3921 | 2 |  | MRP+EF− | 4 | + | + | #[c] | − |
| 3977 | 2 |  | MRP+EF− | 2 | + | + | # | − |
| 3889 | 2 |  | MRP−EF− | 6 | + | + | + | + |
| T-15 | 2 |  | MRP−EF− | 6 | + | + | + | + |
| 4961 | 3 | R |  | 0 | ND[d] | ND | ND | − |
| 6407 | 4 | R |  | 4 | + | + | + | − |
| 11538 | 5 | R |  | 4 | + | + | # | − |
| 2524 | 6 | R |  | 2 | + | + | # | − |
| 8074 | 7 | R |  | 0 | ND | ND | ND | − |
| 10681 | 7 |  |  | 0 | ND | ND | ND | − |
| 10727 | 7 |  |  | 0 | ND | ND | ND | − |
| 14391 | 7 |  |  | 2 | ND | ND | ND | − |
| 14636 | 8 | R |  | 5 | + | + | + | − |
| NV92109 | 8 |  |  | 3 | + | + | # | − |
| 22083 | 9 | R |  | 0 | ND | ND | ND | − |
| 220891KM | 9 |  |  | 3 | + | + | # | − |
| 4417 | 10 | R |  | 2 | + | + | # | + |
| 12814 | 11 | R |  | 2 | + | + | # | − |
| 8830 | 12 | R |  | 0 | ND | ND | ND | − |
| 10581 | 13 | R |  | 2 | + | + | # | − |
| 13730 | 14 | R |  | 6 | + | + | + | + |
| 220891GV | 14 |  |  | 6 | + | + | + | + |
| T639 | 15 | R |  | 6 | + | + | + | + |
| 2726 | 16 | R |  | 0 | ND | ND | ND | − |
| 93A | 17 | R |  | 4 | + | + | + | − |
| NT77 | 18 | R |  | 6 | + | + | + | + |
| 42A | 19 | R |  | 3 | + | + | + | + |
| 865192 | 20 | R |  | 0 | ND | ND | ND | − |
| 14A | 21 | R |  | 0 | ND | ND | ND | − |
| 88/1861 | 22 | R |  | 2 | + | + | # | − |

[a]For the type 2 strains, the phenotypes as described by Vecht et al, Infect. Immun., 59:3156–3162 (1991) and by Vecht et al., Infect. Immun., 60:550–556 (1992) are presented.
[b]Titration of hemolytic activity, inhibition of hemolytic activity by 0.1% cholesterol, the reversible inactivation of hemolytic activity by incubation with $H_2O_2$ and β-mercaptoethanol, inhibition of hemolytic activity by specific pig serum P399, and immunoblotting using specific mouse serum M189, were done as described in materials and methods.
[c]#= test performed but no result because of too low hemolytic activity (see text).
[d]ND = not determined

TABLE 3

Effect of immunization with different vaccines on survival rate of mice challenged intraperitoneally with *S. suis* strain P1/7.

| Vaccin | survival rate |
|---|---|
| VAC-CCS[a] | 9/9 |
| VAC-SCF[b] | 6/10 |
| VAC-SLY[c] | 10/10 |
| Placebo | 0/10 |

[a]vaccine containing concentrated culture supernatant
[b]vaccine containing Superose column fractions 19–31.
[c]vaccine containing purified suilysin.

TABLE 4

Summarizing table showing total numerical clinical scores at day of challenge and day 1–7 post challenge.

| vaccine | clinical score at post challenge day | | | | | | | | |
|---|---|---|---|---|---|---|---|---|---|
|  | 0 | 1[a] | 2[a] | 3[a] | 4[a] | 5 | 6 | 7 | total |
| VAC-SLY | 0 | 3.7 | 3 | 1.7 | 0.8 | 0.3 | 0.3 | 0.3 | 10.2 |
| VAC-SCF | 0 | 4.7 | 4.2 | 5.5 | 5.5 | 5 | 4.7 | 4.7 | 34.3 |
| PLACEBO | 0 | 5.7 | 5.8 | 6 | 7.8 | 7.7 | 7.3 | 7.7 | 48 |

[a]The scores at day 1–4 represent the mean of two examinations (AM and PM).

TABLE 5

Summarizing table showing clinical signs at day of dissection, macroscopical observations at dissection, reisolation data, and number of cases of meningitis.

| Vaccine | dissection at day post-challenge | arthritis total score | reisolation total score | meningitis |
|---|---|---|---|---|
| VAC-SLY | 7 | 3.5 | 0 | 0 |
| VAC-SCF | 7 | 8 | 7 | 2 |
| PLACEBO | 4 | 12 | 9 | 2 |

FIG. 2: Emulsion profile of Superose-12 chromatography of concentrated culture supernatant of *S. suis* type 2 strain P1/7. Solid line; absorption at 280 nm, dashed line; haemolysin titer.

FIG. 3: Western blot of marker proteins (lane A), concentrated culture supernatant of strain P1/7 (lane B), and of Superose-12 column fractions (lanes C-N). Lane C: fraction 15, lane D: fraction 18, lane E: fraction 20, lane F: fraction 23, lane G: fraction 26, lane H: fraction 28, lane I: fraction 30, lane J: fraction 32, lane K: fraction 34, lane L: fraction 36, lane M: fraction 38, lane N: fraction 40.

TABLE 6

Results of mouse heterologous protection experiment
Groups of 15 mice were vaccinated once subcutaneously with 0.4 ml of different vaccines in GNE adjuvant. Four weeks after vaccination the mice were challenged intraperitoneally with 0.5 ml of a six hours culture of strain P1/7 or strain B10 containing $3 \times 10^9$ bacteria/ml.
Just before challenge bloodsamples were taken and pooled group sera were tested in an immunoblot for anti-SLY or anti-EF antibodies using culture supernatant of strain P1/7 or B10 as antigen.

| vaccine containing | results after P1/7 challenge mortality | results after B10 challenge mortality | results after B10 challenge disease index[a] at day 3 post chal. | presence of SLY in vaccine using SDS-PAGE and Coomassie stain | presence of anti-SLY in pooled group serum in immunoblot using antigen P1/7 sup. | presence of anti-SLY in pooled group serum in immunoblot using antigen B10 sup. | presence of EF in vaccine using SDS-PAGE and Coomassie stain | presence of anti-EF in pooled group serum in immunoblot using antigen P1/7 sup. | presence of anti-EF in pooled group serum in immunoblot using antigen B10 sup. |
|---|---|---|---|---|---|---|---|---|---|
| B10 sup. | 4 | 1 | 3 | ++ | ++ | +++ | − | − | − |
| P1/7 sup. | 9 | 0 | 0 | + | + | ++ | ++ | + | − |
| P1/7 EF | 14 | 1 | 17 | − | − | − | +++ | + | − |
| controls | 15 | 3 | 21 | − | − | − | − | − | − |

[a](no. of dead mice × 3) + (no. of diseased mice × 1)

Legend to the Figures

FIG. 1: SDS-PAGE of low molecular weight markers ((lane A), concentrated culture supernatant (lane B), purified *Streptococcus suis* haemolysin (lane C), and high molecular weight markers. The gel was stained with Coomassie Brilliant Blue. The numbering on the left and right refers to the molecular weight of the marker proteins.

Marker proteins (lane A) were stained with Coomassie Brilliant Blue. *S. suis* antigens (lanes B–N) were probed with rabbit serum and then stained by using goat-anti-rabbit conjugate and di-amino benzidine as a substrate. Molecular weights of marker proteins are indicated on the left.

I claim:

1. A polypeptide of *Streptococcus suis* having a molecular weight of about 54 kD as determined by SDS-PAGE, which can be activated by thiol, inhibited by cholesterol and has a haemolytic activity when in its native form.

2. The polypeptide of claim 1, having the N-terminal amino acid sequence Asp-Ser-Lys-Gln-Asp-Ile-Asn-Gln-Tyr-Phe-Gln-Ser-Leu-Thr-Tyr-Glu.

3. A vaccine capable of protecting pigs against *Streptococcus suis* infection, comprising a polypeptide according to claim 1 and a pharmaceutically acceptable carrier.

4. The vaccine of claim 3, comprising in addition another *Streptococcus suis* immunogen.

5. The vaccine of claim 3, wherein the polypeptide is coupled to a carrier.

6. The vaccine of claim 5, wherein the carrier is a capsular polysaccharide.

7. The vaccine of claim 3, further comprising an adjuvant.

8. The vaccine of claim 3, further comprising an additional immunogen derived from a pig pathogenic virus or microorganism.

9. The vaccine of claim 8, wherein the additional immunogen is selected from the group consisting of *Actinobacillus pleuropneumoniae*, Pseudorabies virus, Porcine Influenza virus, Porcine Parvovirus, Transmissible Gastroenteritisvirus, rotavirus, *Escherichia coli*, *Erysipelothrix rhusiopathiae*, *Pasteurella multocida* and *Bordetella bronchiseptica*.

10. An antibody monospecifically reactive with a polypeptide according to claim 1.

11. Method for the preparation of a vaccine capable of protecting mammals against infection by *Streptococcus suis* comprising mixing the polypeptide according to claim 1 with a pharmaceutically acceptable carrier, adjuvant or diluent.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Streptococcus suis
        ( B ) STRAIN: P1/7
        ( C ) INDIVIDUAL ISOLATE: -

( v i i ) IMMEDIATE SOURCE:
  ( B ) CLONE: -

( x i ) SEQUENCE DESCRIPTION: SEQ ID NO: 1:

Asp Ser Lys Gln Asp Ile Asn Gln Tyr Phe Gln Ser Leu Thr Tyr Glu
 1           5                   10                  15